United States Patent
Williams et al.

(12) 
(10) Patent No.: US 10,739,347 B2
(45) Date of Patent: Aug. 11, 2020

(54) FLUORESCENT FUSION PROTEINS FOR USE AS REPORTERS IN MULTIPLEXED BIOASSAYS

(71) Applicant: FUNDAMENTAL SOLUTIONS CORPORATION, Easton, PA (US)

(72) Inventors: M. Russell Williams, Easton, PA (US); Joel Lwande, Athens, OH (US); Shengwen Liang, Athens, OH (US); Kyle McQuaid, Athens, OH (US)

(73) Assignee: Fundamental Solutions Corporation, Easton, PA (US)

(*) Notice: Subject to any disclaimer, the term of this patent is extended or adjusted under 35 U.S.C. 154(b) by 235 days.

(21) Appl. No.: 16/105,303

(22) Filed: Aug. 20, 2018

(65) Prior Publication Data

US 2020/0057072 A1    Feb. 20, 2020

(51) Int. Cl.
| | |
|---|---|
| *G01N 33/58* | (2006.01) |
| *G01N 33/542* | (2006.01) |
| *C12N 9/02* | (2006.01) |

(52) U.S. Cl.
CPC ......... *G01N 33/582* (2013.01); *C12N 9/0069* (2013.01); *C12Y 113/12005* (2013.01); *G01N 33/542* (2013.01); *C07K 2319/60* (2013.01); *G01N 2333/90241* (2013.01)

(58) Field of Classification Search
None
See application file for complete search history.

(56) References Cited

U.S. PATENT DOCUMENTS

| | | | |
|---|---|---|---|
| 9,023,640 B2 | 5/2015 | Williams et al. | |
| 9,752,199 B2 | 9/2017 | Zupancic et al. | |
| 9,850,546 B2 | 12/2017 | Zupancic et al. | |
| 9,850,547 B2 | 12/2017 | Zupancic et al. | |
| 9,850,548 B2 | 12/2017 | Zupancic et al. | |
| 2012/0122127 A1* | 5/2012 | Bavari .............. | G01N 33/6854 435/7.92 |
| 2018/0180608 A1 | 6/2018 | Zupancic et al. | |

OTHER PUBLICATIONS

MacKay et al. Genetics 2003, vol. 163, p. 1365-1373 (Year: 2003).*
Kuno et al. J Biol. Chem 1993, vol. 268, p. 13510-13518 (Year: 1993).*
Ashmun et al. Blood 1992, vol. 79, p. 3344-3349 (Year: 1992).*
Green et al. Pro. Natl. Acad. Sci. 1999 vol. 96, p. 4176-4179 (Year: 1999).*
Erlenbach et al. J. Biol. Chem 2001 vol. 276, p. 29382-29392 (Year: 2001).*
Noutoshi et al. The Plant Journal 2005 vol. 43, p. 873-888 (Year: 2005).*
Bowie et al. Science, 1990 vol. 247:1306-1310 (Year: 1990).*
Xiong et al. Frontiers in Plant Science 2014 vol. 5, p. 1-13 (Year: 2014).*
Xue et al. Angew Chem. Int. Ed. 2017 vol. 56, p. 7112-7116 (Year: 2017).*
Navas-Navarro et al. (Cell Chemical Biology 2016 vol. 23, p. 738-745). (Year: 2016).*
Bakayan, Adil, et al. "Red fluorescent protein-aequorin fusions as improved bioluminescent Ca2+ reporters in single cells and mice." PloS one 6.5 (2011): e19520.
Bakayan, Adil, et al. "Imaging Ca2+ activity in mammalian cells and zebrafish with a novel red-emitting aequorin variant." Pflügers Archiv-European Journal of Physiology 467.9 (2015): 2031-2042.
Baubet, Valérie, et al. "Chimeric green fluoreschent protein-aequorin as bioluminescent Ca2+ reporters at the single-cell level." Proceedings of the National Academy of Sciences 97.13 (2000): 7260-7265.
U.S. Appl. No. 62/572,617, entitled "Living Cell-Based Biosensor for Rapid Pathogen Detection," filed Oct. 16, 2017.
U.S. Appl. No. 62/643,378, entitled "Programmable Immunocyte Receptor Complex System," filed Mar. 15, 2018.
U.S. Appl. No. 62/651,916, entitled "Programmable Immunocyte Receptor Complex System," filed Apr. 3, 2018.

* cited by examiner

*Primary Examiner* — Changhwa J Cheu
(74) *Attorney, Agent, or Firm* — Frost Brown Todd LLC (57) ABSTRACT

A bioassay for the detection of multiple target analytes that includes living immunocytes of a plurality of predetermined types; a signal-generating reporter within each immunocyte that is responsive to predetermined changes occurring within the immunocyte and that includes a bioluminescent protein linked to a fluorescent protein; a signal transduction pathway associated with each signal-generating reporter that is operative to induce the predetermined changes within each immunocyte; a detector element associated with the signal transduction pathway that is operative to trigger the signal transduction pathway; an analyte binding element associated with the detector element that is specific to both the detector element and a target analyte; and wherein upon the binding of an analyte binding element to which a target analyte is also bound to the detector element, the detector element triggers the signal transduction pathway causing the predetermined changes to occur within the living biological cell, thereby causing the signal-generating reporter to generate a detectable signal.

20 Claims, 2 Drawing Sheets
Specification includes a Sequence Listing.

SEQUENCE LISTING

<160> NUMBER OF SEQ ID NOS: 4

<210> SEQ ID NO 1
<211> LENGTH: 1329
<212> TYPE: DNA
<213> ORGANISM: Artificial Sequence
<220> FEATURE:
<223> OTHER INFORMATION: DNA sequence for Aeq-eGFP (fusion protein)

<400> SEQUENCE: 1

```
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctaccccga ccacatgaag     240
```

```
cagcacgact tcttcaagtc cgccatgccc gaaggctacg tccaggagcg caccatcttc      300
ttcaaggacg acggcaacta caagacccgc gccgaggtga agttcgaggg cgacaccctg      360
gtgaaccgca tcgagctgaa gggcatcgac ttcaaggagg acggcaacat cctggggcac      420
aagctggagt acaactacaa cagccacaac gtctatatca tggccgacaa gcagaagaac      480
ggcatcaagg ccaacttcaa gatccgccac aacatcgagg acggcagcgt gcagctcgcc      540
gaccactacc agcagaacac ccccatcggc gacggccccg tgctgctgcc cgacaaccac      600
tacctgagca cccagtccgc cctgagcaaa gaccccaacg agaagcgcga tcacatggtc      660
ctgctggagt tcgtgaccgc cgccgggatc actctcggca tggacgagct gtacaagtcc      720
ggcgggagcg gatccggcgg ccagtccgga ctcagatctg tcaagcttac atcagacttc      780
gacaacccaa gatggattgg acgacacaag catatgttca atttccttga tgtcaaccac      840
aatggaaaaa tctctcttga cgagatggtc tacaaggcat ctgatattgt catcaataac      900
cttggagcaa cacctgagca agccaaacga cacaaagatg ctgtagaagc cttcttcgga      960
ggagctggaa tgaaatatgg tgtggaaact gattggcctg catatattga aggatggaaa     1020
aaattggcta ctgatgaatt ggagaaatac gccaaaaacg aaccaacgct catccgtata     1080
tggggtgatg ctttgtttga tatcgttgac aaagatcaaa atggagccat tacactggat     1140
gaatggaaag catacaccaa agctgctggt atcatccaat catcagaaga ttgcgaggaa     1200
acattcagag tgtgcgatat tgatgaaagt ggacaactcg atgttgatga gatgacaaga     1260
caacatttag gattttggta caccatggat cctgcttgcg aaaagctcta cggtggagct     1320
gtcccctaa                                                             1329

<210> SEQ ID NO 2
<211> LENGTH: 442
<212> TYPE: PRT
<213> ORGANISM: Artificial Sequence
<220> FEATURE:
<223> OTHER INFORMATION: Amino Acid sequence for Aeq-eGFP (fusion
      protein)

<400> SEQUENCE: 2

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160
```

```
Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Ser
225                 230                 235                 240

Gly Gly Ser Gly Ser Gly Gly Gln Ser Gly Leu Arg Ser Val Lys Leu
                245                 250                 255

Thr Ser Asp Phe Asp Asn Pro Arg Trp Ile Gly Arg His Lys His Met
            260                 265                 270

Phe Asn Phe Leu Asp Val Asn His Asn Gly Lys Ile Ser Leu Asp Glu
        275                 280                 285

Met Val Tyr Lys Ala Ser Asp Ile Val Ile Asn Asn Leu Gly Ala Thr
    290                 295                 300

Pro Glu Gln Ala Lys Arg His Lys Asp Ala Val Glu Ala Phe Phe Gly
305                 310                 315                 320

Gly Ala Gly Met Lys Tyr Gly Val Glu Thr Asp Trp Pro Ala Tyr Ile
                325                 330                 335

Glu Gly Trp Lys Lys Leu Ala Thr Asp Glu Leu Glu Lys Tyr Ala Lys
            340                 345                 350

Asn Glu Pro Thr Leu Ile Arg Ile Trp Gly Asp Ala Leu Phe Asp Ile
        355                 360                 365

Val Asp Lys Asp Gln Asn Gly Ala Ile Thr Leu Asp Glu Trp Lys Ala
    370                 375                 380

Tyr Thr Lys Ala Ala Gly Ile Ile Gln Ser Ser Glu Asp Cys Glu Glu
385                 390                 395                 400

Thr Phe Arg Val Cys Asp Ile Asp Glu Ser Gly Gln Leu Asp Val Asp
                405                 410                 415

Glu Met Thr Arg Gln His Leu Gly Phe Trp Tyr Thr Met Asp Pro Ala
            420                 425                 430

Cys Glu Lys Leu Tyr Gly Gly Ala Val Pro
        435                 440
```

<210> SEQ ID NO 3
<211> LENGTH: 1976
<212> TYPE: DNA
<213> ORGANISM: Artificial Sequence
<220> FEATURE:
<223> OTHER INFORMATION: DNA sequence for Aeq- tdTomato (fusion protein)

<400> SEQUENCE: 3

```
atggtgagca agggcgagga ggtcatcaaa gagttcatgc gcttcaaggt gcgcatggag      60
ggctccatga acggccacga gttcgagatc gagggcgagg cgagggccg ccctacgag       120 ggcacccaga ccgccaagct gaaggtgacc aagggcggcc ccctgccctt cgcctgggac     180
atcctgtccc cccagttcat gtacggctcc aaggcgtacg tgaagcaccc cgccgacatc     240
cccgattaca agaagctgtc cttccccgag ggcttcaagt gggagcgcgt gatgaacttc     300
gaggacggcg gtctggtgac cgtgacccag gactcctccc tgcaggacgg cacgctgatc     360
tacaaggtga agatgcgcgg caccaacttc ccccccgacg gccccgtaat gcagaagaag     420
```

```
accatgggct gggaggcctc caccgagcgc ctgtacccccc gcgacggcgt gctgaagggc    480
gagatccacc aggccctgaa gctgaaggac ggcggccact acctggtgga gttcaagacc    540
atctacatgg ccaagaagcc cgtgcaactg cccggctact actacgtgga caccaagctg    600
gacatcacct cccacaacga ggactacacc atcgtggaac agtacgagcg ctccgagggc    660
cgccaccacc tgttcctggg catggcaccg gcagcaccg gcagcggcag ctccggcacc    720
gcctcctccg aggacaacaa catggccgtc atcaaagagt tcatgcgctt caaggtgcgc    780
atggagggct ccatgaacgg ccacgagttc gagatcgagg gcgagggcga gggccgcccc    840
tacgagggca cccagaccgc caagctgaag gtgaccaagg gcggcccct gcccttcgcc    900
tgggacatcc tgtcccccca gttcatgtac ggctccaagg cgtacgtgaa gcaccccgcc    960
gacatccccg attacaagaa gctgtccttc cccgagggct tcaagtggga gcgcgtgatg   1020
aactcaaggt gaagatgcgc ggcaccaact ccccccccga cggccccgta atgcagaaga   1080
agaccatggg ctgggaggcc tccaccgagc gcctgtaccc ccgcgacggc gtgctgaagg   1140
gcgagatcca ccaggccctg aagctgaagg acggcggcca ctacctggtg gagttcaaga   1200
ccatctacat ggccaagaag cccgtgcaac tgcccggcta ctactacgtg gacaccaagc   1260
tggacatcac ctcccacaac gaggactaca ccatcgtgga acagtacgag cgctccgagg   1320
gccgccacca cctgttcctg tacggcatgg acgagctgta caagtccggc gggagcggat   1380
ccggcggcca gtccggactc agatctgtca agcttacatc agacttcgac aacccaagat   1440
ggattggacg acacaagcat atgttcaatt tccttgatgt caaccacaat ggaaaaatct   1500
ctcttgacga gatggtctac aaggcatctg atattgtcat caataacctt ggagcaacac   1560
tgagcaagc caaacgacac aaagatgctg tagaagcctt cttcggagga gctggaatga   1620
aatatggtgt ggaaactgat tggcctgcat atattgaagg atggaaaaaa ttggctactg   1680
atgaattgga gaaatacgcc aaaaacgaac caacgctcat ccgtatatgg ggtgatgctt   1740
tgtttgatat cgttgacaaa gatcaaaatg agccattac actggatgaa tggaaagcat   1800
acaccaaagc tgctggtatc atccaatcat cagaagattg cgaggaaaca ttcagagtgt   1860
gcgatattga tgaaagtgga caactcgatg ttgatgagat gacaagacaa catttaggat   1920
tttggtacac catggatcct gcttgcgaaa agctctacgg tggagctgtc ccctaa       1976
```

<210> SEQ ID NO 4
<211> LENGTH: 679
<212> TYPE: PRT
<213> ORGANISM: Artificial Sequence
<220> FEATURE:
<223> OTHER INFORMATION: Amino Acid sequence for Aeq- tdTomato (fusion
      protein)

<400> SEQUENCE: 4

```
Met Val Ser Lys Gly Glu Glu Val Ile Lys Glu Phe Met Arg Phe Lys
1               5                   10                  15

Val Arg Met Glu Gly Ser Met Asn Gly His Glu Phe Glu Ile Glu Gly
            20                  25                  30

Glu Gly Glu Gly Arg Pro Tyr Glu Gly Thr Gln Thr Ala Lys Leu Lys
        35                  40                  45

Val Thr Lys Gly Gly Pro Leu Pro Phe Ala Trp Asp Ile Leu Ser Pro
    50                  55                  60

Gln Phe Met Tyr Gly Ser Lys Ala Tyr Val Lys His Pro Ala Asp Ile
65                  70                  75                  80

Pro Asp Tyr Lys Lys Leu Ser Phe Pro Glu Gly Phe Lys Trp Glu Arg
```

```
                       85                  90                  95
        Val Met Asn Phe Glu Asp Gly Gly Leu Val Thr Val Thr Gln Asp Ser
                        100                 105                 110

Ser Leu Gln Asp Gly Thr Leu Ile Tyr Lys Val Lys Met Arg Gly Thr
                        115                 120                 125

Asn Phe Pro Pro Asp Gly Pro Val Met Gln Lys Lys Thr Met Gly Trp
                        130                 135                 140

Glu Ala Ser Thr Glu Arg Leu Tyr Pro Arg Asp Gly Val Leu Lys Gly
        145                 150                 155                 160

Glu Ile His Gln Ala Leu Lys Leu Lys Asp Gly Gly His Tyr Leu Val
                        165                 170                 175

Glu Phe Lys Thr Ile Tyr Met Ala Lys Lys Pro Val Gln Leu Pro Gly
                        180                 185                 190

Tyr Tyr Tyr Val Asp Thr Lys Leu Asp Ile Thr Ser His Asn Glu Asp
                        195                 200                 205

Tyr Thr Ile Val Glu Gln Tyr Glu Arg Ser Glu Gly Arg His His Leu
                        210                 215                 220

Phe Leu Gly His Gly Thr Gly Ser Thr Gly Ser Gly Ser Ser Gly Thr
        225                 230                 235                 240

Ala Ser Ser Glu Asp Asn Asn Met Ala Val Ile Lys Glu Phe Met Arg
                        245                 250                 255

Phe Lys Val Arg Met Glu Gly Ser Met Asn Gly His Glu Phe Glu Ile
                        260                 265                 270

Glu Gly Glu Gly Glu Gly Arg Pro Tyr Glu Gly Thr Gln Thr Ala Lys
                        275                 280                 285

Leu Lys Val Thr Lys Gly Gly Pro Leu Pro Phe Ala Trp Asp Ile Leu
                        290                 295                 300

Ser Pro Gln Phe Met Tyr Gly Ser Lys Ala Tyr Val Lys His Pro Ala
        305                 310                 315                 320

Asp Ile Pro Asp Tyr Lys Lys Leu Ser Phe Pro Glu Gly Phe Lys Trp
                        325                 330                 335

Glu Arg Val Met Asn Phe Glu Asp Gly Gly Leu Val Thr Val Thr Gln
                        340                 345                 350

Asp Ser Ser Leu Gln Asp Gly Thr Leu Ile Tyr Lys Val Lys Met Arg
                        355                 360                 365

Gly Thr Asn Phe Pro Pro Asp Gly Pro Val Met Gln Lys Lys Thr Met
                        370                 375                 380

Gly Trp Glu Ala Ser Thr Glu Arg Leu Tyr Pro Arg Asp Gly Val Leu
        385                 390                 395                 400

Lys Gly Glu Ile His Gln Ala Leu Lys Leu Lys Asp Gly Gly His Tyr
                        405                 410                 415

Leu Val Glu Phe Lys Thr Ile Tyr Met Ala Lys Lys Pro Val Gln Leu
                        420                 425                 430

Pro Gly Tyr Tyr Tyr Val Asp Thr Lys Leu Asp Ile Thr Ser His Asn
                        435                 440                 445

Glu Asp Tyr Thr Ile Val Glu Gln Tyr Glu Arg Ser Glu Gly Arg His
                        450                 455                 460

His Leu Phe Leu Tyr Gly Met Asp Glu Leu Tyr Lys Ser Gly Gly Ser
        465                 470                 475                 480

Gly Ser Gly Gly Gln Ser Gly Leu Arg Ser Val Lys Leu Thr Ser Asp
                        485                 490                 495

Phe Asp Asn Pro Arg Trp Ile Gly Arg His Lys His Met Phe Asn Phe
                        500                 505                 510
```

```
Leu Asp Val Asn His Asn Gly Lys Ile Ser Leu Asp Glu Met Val Tyr
            515                 520                 525
Lys Ala Ser Asp Ile Val Ile Asn Asn Leu Gly Ala Thr Pro Glu Gln
        530                 535                 540
Ala Lys Arg His Lys Asp Ala Val Glu Ala Phe Phe Gly Gly Ala Gly
545                 550                 555                 560
Met Lys Tyr Gly Val Glu Thr Asp Trp Pro Ala Tyr Ile Glu Gly Trp
                565                 570                 575
Lys Lys Leu Ala Thr Asp Glu Leu Glu Lys Tyr Ala Lys Asn Glu Pro
            580                 585                 590
Thr Leu Ile Arg Ile Trp Gly Asp Ala Leu Phe Asp Ile Val Asp Lys
            595                 600                 605
Asp Gln Asn Gly Ala Ile Thr Leu Asp Glu Trp Lys Ala Tyr Thr Lys
        610                 615                 620
Ala Ala Gly Ile Ile Gln Ser Ser Glu Asp Cys Glu Glu Thr Phe Arg
625                 630                 635                 640
Val Cys Asp Ile Asp Glu Ser Gly Gln Leu Asp Val Asp Glu Met Thr
                645                 650                 655
Arg Gln His Leu Gly Phe Trp Tyr Thr Met Asp Pro Ala Cys Glu Lys
            660                 665                 670
Leu Tyr Gly Gly Ala Val Pro
            675
```

FLUORESCENT FUSION PROTEINS FOR USE AS REPORTERS IN MULTIPLEXED BIOASSAYS

REFERENCE TO A SEQUENCE LISTING

A sequence listing in computer readable form (CRF) is on file. The sequence listing is in an ASCII text (.txt) file entitled SEQ ID NO 1-4_ST25.txt created on Aug. 15, 2018 and is 15 KB in size. The sequence listing is incorporated by reference as if fully recited herein.

BACKGROUND OF THE INVENTION

The present invention is directed in general toward bioassays, biosensors, and cell-based assays, and more specifically to systems and system components that include living, engineered immunocytes that express fluorescent fusion reporter proteins for use in multiplexed bioassays for the detection of target analytes.

Biosensor systems such as those disclosed in U.S. Pat. Nos. 9,023,640; 9,752,199; 9,850,546; 9,850,547; and 9,850,548; and U.S. patent application Ser. Nos. 15/848,104; and 62/572,617, all of which are incorporated by reference herein, in their entirety, for all purposes, may include the following elements or components: (i) a living biological cell of a predetermined type (e.g., an engineered immunocyte); (ii) a signal-generating reporter within the living biological cell, wherein the signal-generating reporter is responsive to predetermined changes occurring within the living biological cell; (iii) a signal transduction pathway or activator mechanism associated with the signal-generating reporter, wherein the signal transduction pathway or activator mechanism is operative to induce the predetermined changes within the living biological cell; (iv) a universal detector element (e.g., a transmembrane, non-antibody fusion protein expressed by the living immunocyte) associated with the activator mechanism, wherein the universal detector element is operative to trigger the activator mechanism; (v) an analyte binding element (e.g., a soluble antibody) associated with the universal detector element, wherein the analyte binding element is specific to both the universal detector element and a target analyte; and (vi) wherein upon the binding of an analyte binding element to which a target analyte is also bound to the universal detector element, the universal detector element triggers the activator mechanism causing the predetermined changes to occur within the living biological cell, thereby causing the signal-generating reporter to generate a detectable signal. In such systems, the detectable signal may be a flash of visible light. Additionally, transmembrane, non-antibody fusion proteins expressed by the living immunocyte in such systems may include (a) at least one component of a protein that is adapted to bind to the analyte binding element (e.g., a bacterial binding protein or antibody binding domain derived from an Fc receptor protein); and (b) at least one component of a receptor complex normally expressed on the surface of the immunocyte (e.g., IgM; Igα/β; IgE; CD19; or CD3).

Other detection systems such as those described in U.S. Patent Application Nos. 62/643,378; and 62/651,916, which are incorporated by reference herein, in their entirety, for all purposes, may include the following elements or components: (i) a programmable receptor complex expressed by a living, engineered immunocyte (e.g., CD4+ T cell, CD8+ T cell, γδ T cell, or allogeneic cell); (ii) wherein the programmable receptor complex includes a plurality of native or endogenously-expressed receptor subunits (e.g., T cell receptor subunits such as CD3-epsilon, CD3-delta, CD3-gamma, TCR alpha, TCR beta, and CD3-zeta); (iii) wherein at least one of the plurality of native or endogenously-expressed receptor subunits has been engineered or modified to include either a biotin-binding component (e.g., monomeric streptavidin 2 or enhanced monoavidin) or an FcγRI receptor component; and (v) wherein the biotin-binding component or FcγRI receptor component is operative to bind to a target detector molecule that binds to or otherwise interacts with a predetermined target. Such detection systems have diagnostic applications and may also include within the living, engineered immunocyte a signal-generating reporter that emits a detectable signal upon binding to a target analyte.

While the systems described above are highly effective for their intended purposes, the signal-generating reporter included therein is capable of reporting only a single type of binding event. This aspect of the systems described above limits the use of these detection systems and makes them unsuitable for multiplexing applications that are directed toward the detection of multiple targets or multiple types of binding events. Accordingly, there is a need for a single biosensor system or single living-cell based detection system that can simultaneously detect the binding of different types of targets, or that can simultaneously detect different types of binding events, under the same test conditions.

SUMMARY OF THE INVENTION

The following provides a summary of certain exemplary embodiments of the present invention. This summary is not an extensive overview and is not intended to identify key or critical aspects or elements of the present invention or to delineate its scope. However, it is to be understood that the use of indefinite articles in the language used to describe and claim the present invention is not intended in any way to limit the described system. Rather the use of "a" or "an" should be interpreted to mean "at least one" or "one or more".

In accordance with one aspect of the present invention, a first bioassay for the detection of multiple target analytes is provided. This bioassay includes living biological cells of a plurality of predetermined types; a signal-generating reporter within each of the living biological cells that is responsive to predetermined changes occurring within the living biological cell, and that includes a bioluminescent protein linked to a fluorescent protein by a linker of a predetermined length; a signal transduction pathway or activator mechanism associated with each signal-generating reporter that is operative to induce the predetermined changes within each living biological cell; a detector element associated with the signal transduction pathway or activator mechanism that is operative to trigger the signal transduction pathway or activator mechanism; an analyte binding element associated with the detector element that is specific to both the detector element and a target analyte; and wherein upon the binding of an analyte binding element to which a target analyte is also bound to the detector element, the detector element triggers the signal transduction pathway or activator mechanism causing the predetermined changes to occur within the living biological cell, thereby causing the signal-generating reporter to generate a detectable signal.

In accordance with another aspect of the present invention, a second bioassay for the detection of multiple target analytes is provided. This bioassay includes living immunocytes of a plurality of predetermined types; a signal-generating reporter within each of the living immunocytes that is responsive to predetermined changes occurring within the immunocyte and that includes a bioluminescent protein linked to a fluorescent protein by a linker of a predetermined length; a signal transduction pathway or activator mechanism associated with each signal-generating reporter that is operative to induce the predetermined changes within each living immunocyte; a detector element associated with the signal transduction pathway or activator mechanism that is operative to trigger the signal transduction pathway or activator mechanism; an analyte binding element associated with the detector element that is specific to both the detector element and a target analyte; and wherein upon the binding of an analyte binding element to which a target analyte is also bound to the detector element, the detector element triggers the signal transduction pathway or activator mechanism causing the predetermined changes to occur within each living immunocyte, thereby causing the signal-generating reporter to generate a detectable signal.

In yet another aspect of this invention, a signal-generating reporter protein for use in living biological cells is provided. This signal-generating reporter protein is encoded by a DNA sequence having at least 95% identity to the group consisting of SEQ ID NO: 1 and SEQ ID NO: 3.

Additional features and aspects of the present invention will become apparent to those of ordinary skill in the art upon reading and understanding the following detailed description of the exemplary embodiments. As will be appreciated by the skilled artisan, further embodiments of the invention are possible without departing from the scope and spirit of the invention. Accordingly, the drawings and associated descriptions are to be regarded as illustrative and not restrictive in nature.

BRIEF DESCRIPTION OF THE DRAWINGS

The accompanying drawings, which are incorporated into and form a part of the specification, schematically illustrate one or more exemplary embodiments of the invention and, together with the general description given above and detailed description given below, serve to explain the principles of the invention, and wherein.

DETAILED DESCRIPTION OF THE INVENTION

Exemplary embodiments of the present invention are now described with reference to the Figures. Although the following detailed description contains many specifics for the purposes of illustration, a person of ordinary skill in the art will appreciate that many variations and alterations to the following details are within the scope of the invention. Accordingly, the following embodiments of the invention are set forth without any loss of generality to, and without imposing limitations upon, the claimed invention.

The present invention provides bioassay, biosensor, and cell-based systems and system components that include living, engineered immunocytes that express unique fluorescent fusion reporter proteins for use in multiplexed bioassays for the detection of target analytes or of binding events of interest. The systems of this invention involve the use of different receptor complexes and different cell types that may be combined into single test systems or assays that provide significant benefits over systems that do not provide multiplexing capabilities.

Bioluminescence resonance energy transfer (BRET) is a technique that can be used to monitor protein-protein interactions in real time. BRET involves resonance energy transfer between a bioluminescent donor moiety and a fluorescent acceptor moiety. The technique involves heterologous co-expression of fusion proteins, which link proteins of interest to a bioluminescent donor enzyme or acceptor fluorophore. Energy transfer between these proteins is then detected. Energy transfer efficiency is highly dependent on the distance between the donor and acceptor moieties and their relative orientation with respect to each other. In assays that are BRET-based, the typical effective distance between the donor and acceptor is 10 to 100 angstroms (Å). This range correlates well with most biological interactions, thus making BRET an excellent tool for monitoring macromolecular interactions. Because the donor emits photons intrinsically, fluorescence excitation is unnecessary. Therefore, BRET avoids some of the problems inherent in fluorescence resonance energy transfer (FRET) approaches, such as photobleaching, autofluorescence, and undesirable stimulation of photobiological processes.

The bioassays of the present invention include a multiplexing system that utilizes unique fusion proteins that are expressed by living immunocytes, such as for example B-cells and T-cells such as those used in the previously described biosensor systems and programmable immunocyte systems. In the present invention, BRET utilizes the natural chemical light emitting properties of Aequorin to excite attached fluorescent proteins, such as enhanced GFP (eGFP) or tandem dimer Tomato (tdTomato), thereby changing the color properties of the emitted light. See, for example, Bakayan A., Vaquero C. F., Picazo F. and Llopis J. (2011): *Red Fluorescent Protein Aequorin Fusions as Improved Bioluminescent $Ca^{2+}$ Reporters in Single Cells and Mice*. PLoS ONE6(5): e19520. https://doi.org/10.1371/journal.pone.0019520; Bakayan A., Domingo B., Miyawaki A. and Llopis J. (2015): *Imaging $Ca^{2+}$ activity in mammalian cells and zebrafish with a novel red-emitting aequorin variant*. Eur J Physiol 467:2031-2042; and Baubet V., Mouellic H., Campbell A. K., Lucas-Meunier E, Fossier P. and Brulet P. (2000): *Chimeric green fluorescent protein-aequorin as bioluminescent $Ca^{2+}$ reporters at the single-cell level*. PNAS 97:7260-7265, all of which are incorporated herein by reference in their entirety for all purposes.

The present invention involves the expression of Aequorin-excited Green Fluorescent Protein (Aeq-eGFP; green signal) and Aequorin-tandem dimer Tomato (Aeq-tdTomato: red signal) fusion proteins in Jurkat T cells following transfection thereof. Mouse anti-Human CD3c mAb was used to trigger the calcium signaling cascade in the transfected cells and wavelength filters were used to show the resultant red and green light following BRET. Aspheric lenses were used to adjust the direction of scattered light rays into a regular parallel pattern, which increased the overall effectiveness of the light filters. Cells were cloned by single cell sorting and the most desirable clones were identified for future multiplexing development. All the flash tests were performed using a GloMax Luminometer (Promega). The Aeq-eGFP and Aeq-tdTomato fusion proteins of the present invention were used in the design because their emission wavelengths do not overlap; accordingly, they are compatible with one another. Furthermore, the eGFP protein has been modified through specific mutation to improve its solubility and brightness.

Due to the flexibility of the linker length used with these constructs (see SEQ ID NO: 1-4), the fusion proteins of this invention can be modified to generate new emission wavelengths compatible with additional Aequorin-Fluorescent Protein (Aeq-FP) fusion proteins. The scientific literature teaches that apoaequorin alone is unstable within the cytosol of mammalian cells and has a half-life of approximately 20 minutes, whereas fluorescent proteins are very robust and are likely to stabilize and protect apoaequorin in Aeq-FP fusion proteins. With regard to the Aeq-eGFP fusion protein of this invention, the eGFP acceptor fluorophore is excited by oxycoelenterazine through a radiationless energy transfer. A green light (509 nm) is emitted when the eGFP returns to its ground state. This intermolecular radiationless energy transfer results in increased quantum yield for Aequorin.

The efficiency of the disclosed process is affected by other factors. For example, the emission spectrum of the donor must have the greatest overlap with the excitation spectrum of the acceptor. In addition, the energy transferred also strongly depends on the geometry of the donor and acceptor dipoles (in particular the relative orientation and distance between the two dipoles) and is modulated by their respective motion. In various embodiments of this invention, the length of the linker (14 amino acids) between Aeq and eGFP is optimized for maximum light-emitting activity because the donor and the acceptor dipoles have more freedom to be in a configuration favorable for optimum intramolecular energy transfer. Compared to normal Green Fluorescent Protein (GFP), eGFP is an improvement that was developed by mutating (F64L and S65T) to modify the excitation spectra and enhance fluorescence intensity. eGFP was further modified (V163A) to improve the proper folding of the protein. These mutations greatly improve the fluorescence signal when compared with unmodified GFP due to a higher concentration of properly folded protein.

The Aeq-tdTomato embodiment of this invention exhibits the highest BRET efficiency (i.e., largest energy transfer critical distance) and percentage of photon counts in the red emission band compared to other Aeq-FP fusion proteins analyzed during the development of the fusion proteins disclosed herein. In addition, red fluorophore maturation of Aeq-tdTomato within cells (18 hours after transfection) is faster than that of the other Aeq-FP fusion proteins (30 hours after transfection). Cells expressing Aeq-tdTomato also have brighter fluorescence than those expressing other fusion proteins due to the high molar extinction coefficient of Aeq-tdTomato. Compared to other Aeq-FP fusion proteins, Aeq-tdTomato has high quantum yield resulting in greater overall brightness in the red emission band.

Figure 1:
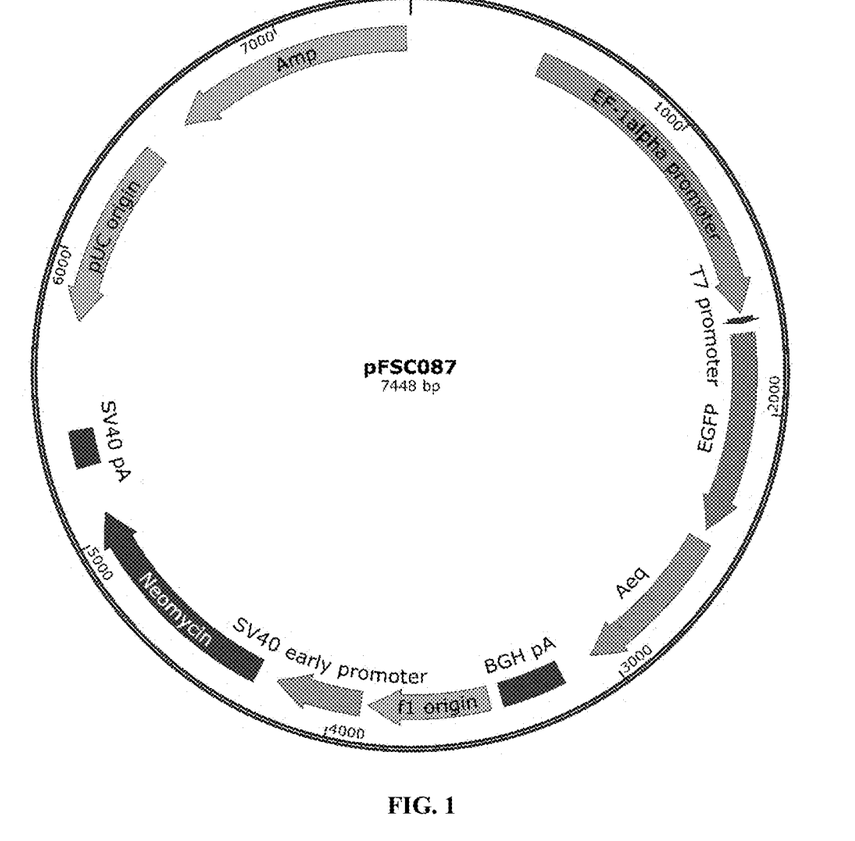
FIG. 1 is an illustration of plasmid pFSC087.

FIG. 1 is an illustration of plasmid pFSC087, which is the Aeq-eGFP expression plasmid. This plasmid includes a jellyfish Aequorin gene fused with an eGFP gene on its N-terminus through a GS linker. The Aeq-eGFP construct is driven by a human EF1α promoter; and a neomycin gene was used as a selection marker. Plasmid features include: an EF1 promoter, an AEQ (aequorin) gene, and an eGFP (enhanced green fluorescent protein) gene. The EF1 promoter is the human elongation factor 1α-subunit (hEF-1a) promoter for high-level expression across a broad range of species and cell types. The Aequorin gene, which encodes a Jellyfish (*Aequorea victoria*) calcium activatable photoprotein, was codon optimized and synthesized by DNA2.0. Active aequorin enzyme is formed by a complex between apoaequorin (APO), oxygen, and externally infused coelenterazine. When apoaequorin binds intracellular calcium released from the endoplasmic reticulum, the enzyme is activated and coelenterazine is oxidized, emitting light and releasing free apoaequorin and coelenteramide. The enhanced green fluorescence protein gene was obtained from pEGFP-C1 vector (Clonetech). The valine 163 of the eGFP was substituted by alanine using mutagenesis to improve the proper folding of the protein and increase the fluorescence. SEQ ID NO. 1 is the DNA sequence for pFSC087 and SEQ ID NO. 2 is the amino acid sequence for pFSC087.

Figure 2:
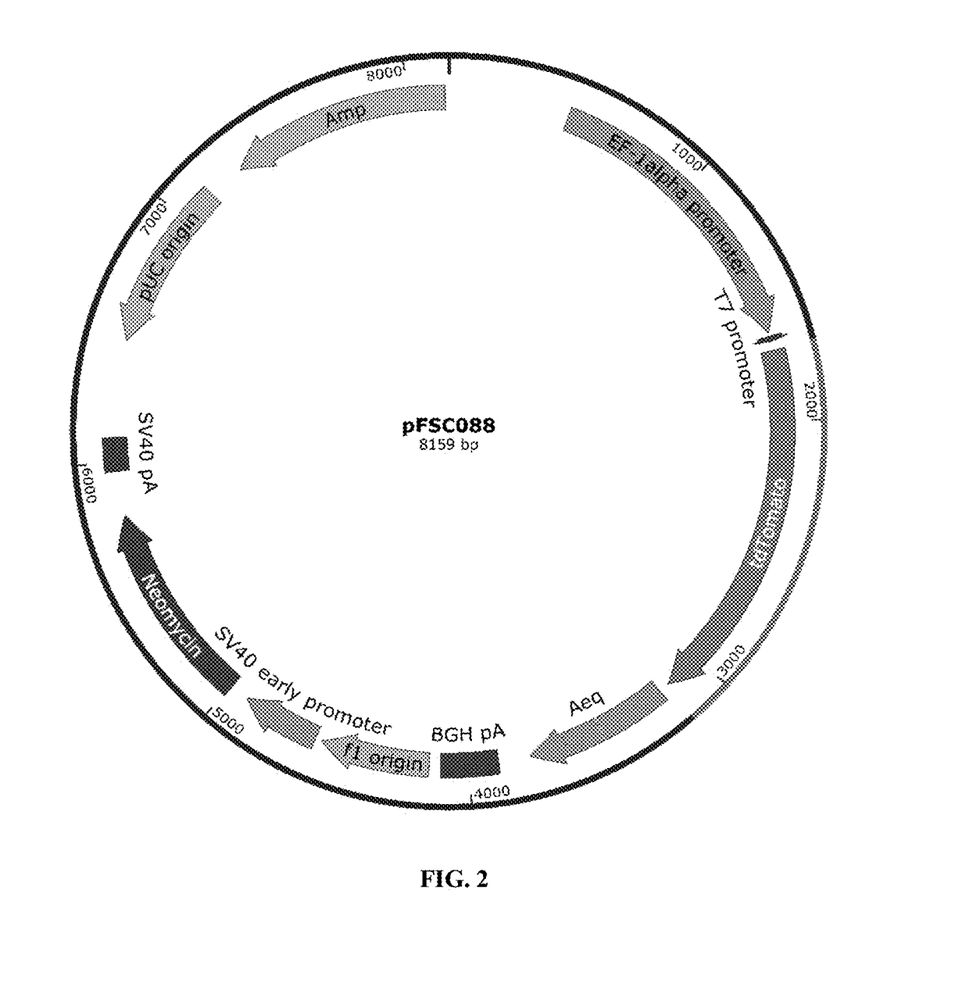
FIG. 2 is an illustration of plasmid pFSC088.

FIG. 2 is an illustration of plasmid pFSC088, which is the Aeq-tdTomato expression plasmid. This plasmid also includes a jelly fish Aequorin gene fused with a tdTomato gene on its N-terminus through a GS linker. The Aeq-tdTomato gene construct is driven by a human EF1α promoter; and a neomycin gene was used as a selection marker. Plasmid features include: an EF1 promoter, an AEQ (Aequorin) gene, and a tdTomato gene (tandem dimer Tomato) gene. As previously described, the EF1 promoter is the human elongation factor 1α-subunit (hEF-1a) promoter for high-level expression across a broad range of species and cell types. The Aequorin gene, which encodes a Jellyfish (*Aequorea victoria*) calcium activatable photoprotein, was codon optimized and synthesized by DNA2.0. Active aequorin enzyme is formed by a complex between apoaequorin (APO), oxygen, and externally infused coelenterazine. When apoaequorin binds intracellular calcium released from the endoplasmic reticulum, the enzyme is activated and coelenterazine is oxidized, emitting light and releasing free apoaequorin and coelenteramide. The tdTomato gene is obtained from the ptdTomato-C1 vector (Clonetech). tdTomato is a genetic fusion of two copies of the dTomato gene which was specifically designed for low aggregation, and its tandem dimer structure plays an important role in the exceptional brightness of tdTomato. SEQ ID NO. 3 is the DNA sequence for pFSC088 and SEQ ID NO. 4 is the amino acid sequence for pFSC088.

Multiplexing Testing Protocol

With regard to the present invention, Bioluminescence Resonance Energy Transfer (BRET) was employed to utilize the natural chemical light emitting properties of Aequorin to excite attached fluorescent proteins, such as eGFP or tdTomato, thereby changing the color properties of the emitted light. This invention involves the expression of Aeq-eGFP and Aeq-tdTomato fusion proteins in Jurkat T cells following the transfection thereof. Mouse anti-Human CD3c mAb was used to trigger the calcium signaling cascade in transfected cells and wavelength filters were used to show the resultant red and green light following BRET. Aspheric lenses were used to adjust the direction of scattered light rays into a regular parallel pattern, which increased the effectiveness of the light filters. Cells were cloned by single cell sorting and the most desirable clones were identified for multiplexing applications. Selected cells were charged with 1.5 µM Coelenterazine H. Digitionin (0.87 µM) was used to verify the presence of fluorescent proteins within the cells. Bioluminescence resonance energy transfer (BRET) was verified using mouse anti-Human CD3c combined with various light filters. All flash tests were performed in a Promega Glomax 20/20 Luminometer.

More specifically, the materials used in an exemplary embodiment of the multiplexing testing protocol of the present invention include the following (i) Jurkat cells containing the described fluorescent protein constructs at 400,000 Cells/180 µL; (ii) Mouse Anti-Human CD3c Antibody (Biolegend-Cat: 317302); (iii) RPMI 1640 (Gibco-Cat: A10491-01) with 1% (w/v) Bovine Serum Albumin (Seradigm-Cat:1500-500); (iv) Promega Glomax 20/20 Luminometer with Eppendorf tube holder; (v) Laptop with GloMax SIS V1.10.0 software installed; (vi) Blue Wavelength Filter (Omega Optical-Cat: 430BP530); (vii) Green Wavelength Filter (Omega Optical-Cat: 535AF45); (viii) Orange Wavelength Filter (Omega Optical-Cat: 595AF60); (ix) Red Wavelength Filter (Omega Optical-Cat: 640AF20); (x) Aspheric Lens in 1" Lens Holder; (xi) Lens (Newport Optical-Cat: KPA031); and (xii) Holder (Newport Optical-Cat: LT10-10).

An exemplary embodiment of the testing procedure of this invention includes the following steps: (1) connect the GloMax 20/20 Luminometer to the laptop (turn both on); (2) open the GloMax SIS V1.10.0 software; (3) place one of the light filters on top of the sensor inside the GloMax; (4) place the Aspheric lens inside the lens holder, on top of the filter so that the curved side faces down; (5) place the Eppendorf tube holder on top of the lens holder (6) mix 2.1 μL of mouse anti-Human CD3c with 27.9 μL of RPMI with 1% (w/v) BSA in an Eppendorf tube and place the tube inside the Eppendorf tube holder; (7) add 180 μL of cells to the mouse anti-Human CD3c mixture in the GloMax; (8) close the GloMax and start a 2 minute assay; (9) repeat steps 3-8, changing the light filter until all four have been used; and (10) produce a light profile for the cell type of interest.

TABLE 1 below provides an example of a multiplexed bioassay utilizing the engineered immunocytes and fluorescent fusion proteins of the present invention. This assay utilizes six detector cell types and four types of detector antibodies and may be used to screen for four pathogens in one sample: (i) *Pseudomonas*; (ii) *Salmonella*; (iii) *E. coli* O157; and (iv) *E. coli* O111. This multiplexed assay utilizes three fluorescent fusion proteins exhibiting green, red, and blue light. The detector cells are engineered immunocytes that include either an FcγRI receptor component or an enhanced monoavidin receptor component. The detector cells include a fluorescent fusion protein as a reporter that includes Aequorin linked to a green, red, or blue fluorescent protein. The analyte binding elements include Anti-*Pseudomonas* (IgG2a); Anti-*Salmonella* (Biotinylated); Anti-*E. coli* O157 (IgG2a); and Anti-*E. coli* O111. The color of light emitted by each respective cell/target binding event is indicated in the table.

TABLE 1

EXAMPLE OF MULTIPLEX ASSAY.

| | Detector Cell | | | | | |
|---|---|---|---|---|---|---|
| Antibody | FcγRI/GFP | FcγRI/RFP | FcγRI/BFP | eMA/GFP | eMA/RFP | eMA/BFP |
| Anti-*Pseudomonas* (IgG2a) | GREEN | RED | BLUE | | | |
| Anti-*Salmonella* (Biotinylated) | | | | GREEN | RED | BLUE |
| Anti-*E. coli* O157 (IgG2a) | GREEN | RED | BLUE | | | |
| Ant-*E. coli* O111 (Biotinylated) | | | | GREEN | RED | BLUE |

While the present invention has been illustrated by the description of exemplary embodiments thereof, and while the embodiments have been described in certain detail, there is no intention to restrict or in any way limit the scope of the appended claims to such detail. Additional advantages and modifications will readily appear to those skilled in the art. Therefore, the invention in its broader aspects is not limited to any of the specific details, representative devices and methods, and/or illustrative examples shown and described. Accordingly, departures may be made from such details without departing from the spirit or scope of the general inventive concept.

What is claimed:

1. A bioassay for the detection of multiple target analytes, comprising:
    (a) living biological cells of a plurality of predetermined types;
    (b) a signal-generating reporter within each of the living biological cells,
        (i) wherein the signal-generating reporter is responsive to predetermined changes occurring within the living biological cell, and
        (ii) wherein the signal-generating reporter includes a bioluminescent protein linked to a fluorescent protein by a linker of a predetermined length;
    (c) a signal transduction pathway or activator mechanism associated with each signal-generating reporter, wherein the signal transduction pathway or activator mechanism is operative to induce the predetermined changes within each living biological cell;
    (d) a detector element associated with the signal transduction pathway or activator mechanism, wherein the detector element is operative to trigger the signal transduction pathway or activator mechanism;
    (e) an analyte binding element associated with the detector element, wherein the analyte binding element is specific to both the detector element and a target analyte; and
    (f) wherein upon the binding of an analyte binding element, having a target analyte bound thereto, to the detector element, the detector element triggers the signal transduction pathway or activator mechanism causing the predetermined changes to occur within the living biological cell, thereby causing the signal-generating reporter to generate a detectable signal.

2. The bioassay of claim 1, wherein the living biological cells are immunocytes, and wherein the immunocytes are B-cells; T cells; CD4+ T cells; CD8+ T cells; γδ T cells allogeneic cells; or combinations thereof.

3. The bioassay of claim 1, wherein the bioluminescent protein is Aequorin and wherein the fluorescent protein is a green fluorescent protein or a red fluorescent protein.

4. The bioassay of claim 1, wherein the signal-generating reporter protein is encoded by a DNA sequence consisting of SEQ ID NO: 1.

5. The bioassay of claim 1, wherein the signal-generating reporter protein has the amino acid sequence of SEQ ID NO: 2.

6. The bioassay of claim 1, wherein the signal-generating reporter protein is encoded by a DNA sequence consisting of SEQ ID NO: 3.

7. The bioassay of claim 1, wherein the signal-generating reporter protein has the amino acid sequence of SEQ ID NO: 4.

8. The bioassay of claim 1, wherein the signal transduction pathway is a calcium signaling pathway.

9. The bioassay of claim 1, wherein the detector element is a transmembrane, non-antibody fusion protein expressed by the living immunocyte.

10. The bioassay of claim 1, wherein the detector element is a programmable receptor complex that includes a plurality of native or endogenously-expressed receptor subunits.

11. The bioassay of claim 1, wherein the analyte binding element is a soluble antibody.

12. The bioassay of claim 11, wherein the soluble antibody is a soluble IgG.

13. A bioassay for the detection of multiple target analytes, comprising:
    (a) living immunocytes of a plurality of predetermined types;
    (b) a signal-generating reporter within each of the living immunocytes, (i) wherein the signal-generating reporter is responsive to predetermined changes occurring within the immunocyte, and
(ii) wherein the signal-generating reporter includes a bioluminescent protein linked to a fluorescent protein by a linker of a predetermined length;
(c) a signal transduction pathway or activator mechanism associated with each signal-generating reporter, wherein the signal transduction pathway or activator mechanism is operative to induce the predetermined changes within each living immunocyte;
(d) a detector element associated with the signal transduction pathway or activator mechanism, wherein the detector element is operative to trigger the signal transduction pathway or activator mechanism;
(e) an analyte binding element associated with the detector element, wherein the analyte binding element is specific to both the detector element and a target analyte; and
(f) wherein upon the binding of an analyte binding element, having a target analyte bound thereto, to the detector element, the detector element triggers the signal transduction pathway or activator mechanism causing the predetermined changes to occur within living immunocyte, thereby causing the signal-generating reporter to generate a detectable signal.

14. The bioassay of claim 13, wherein the immunocytes are B-cells; T cells; CD4+ T cells; CD8+ T cells; γδ T cells allogeneic cells; or combinations thereof.

15. The bioassay of claim 13, wherein the bioluminescent protein is Aequorin and wherein the fluorescent protein is a green fluorescent protein or a red fluorescent protein.

16. The bioassay of claim 13, wherein the signal-generating reporter protein is encoded by a DNA sequence consisting of SEQ ID NO: 1.

17. The bioassay of claim 13, wherein the signal-generating reporter protein has the amino acid sequence of SEQ ID NO: 2.

18. The bioassay of claim 13, wherein the signal-generating reporter protein is encoded by a DNA sequence consisting of SEQ ID NO: 3.

19. The bioassay of claim 13, wherein the signal-generating reporter protein has the amino acid sequence of SEQ ID NO: 4.

20. A signal-generating reporter protein for use in living biological cells, wherein the signal-generating reporter protein is encoded by a DNA sequence selected from the group consisting of SEQ ID NO: 1 and SEQ ID NO: 3.

* * * * *